US012753404B2

(12) United States Patent
Yang et al.

(10) Patent No.: US 12,753,404 B2
(45) Date of Patent: Oct. 6, 2026

(54) METHOD AND USE FOR CONSTRUCTION OF SEQUENCING LIBRARY BASED ON DNA SAMPLES

(71) Applicant: MGI TECH CO., LTD., Shenzhen (CN)

(72) Inventors: Lin Yang, Shenzhen (CN); Qiwei Wang, Shenzhen (CN); Xinshi Yang, Shenzhen (CN); Yuan Yu, Shenzhen (CN); Juan Yang, Shenzhen (CN); Yanyan Zhang, Shenzhen (CN); Fang Chen, Shenzhen (CN); Hui Jiang, Shenzhen (CN)

(73) Assignee: MGI TECH CO., LTD., Shenzhen (CN)

( * ) Notice: Subject to any disclaimer, the term of this patent is extended or adjusted under 35 U.S.C. 154(b) by 1283 days.

(21) Appl. No.: 17/545,724

(22) Filed: Dec. 8, 2021

(65) Prior Publication Data

US 2022/0090059 A1 Mar. 24, 2022

Related U.S. Application Data

(63) Continuation of application No. PCT/CN2019/092116, filed on Jun. 20, 2019.

(51) Int. Cl.
*C12N 15/10* (2006.01)

(52) U.S. Cl.
CPC ................................ *C12N 15/1068* (2013.01)

(58) Field of Classification Search
None
See application file for complete search history.

(56) References Cited

U.S. PATENT DOCUMENTS

| | | | | |
|---|---|---|---|---|
| 9,677,067 | B2 * | 6/2017 | Toro | C12N 15/1093 |
| 2015/0011396 | A1 | 1/2015 | Schroeder et al. | |
| 2018/0355348 | A1 * | 12/2018 | Adey | C12N 15/1065 |

FOREIGN PATENT DOCUMENTS

| | | | |
|---|---|---|---|
| CN | 103806111 | A | 5/2014 |
| CN | 106497920 | A | 3/2017 |
| CN | 107267596 | A | 10/2017 |
| CN | 109554451 | | 4/2019 |
| WO | 2010148039 | | 12/2010 |
| WO | 2019099081 | | 5/2019 |

OTHER PUBLICATIONS

Tran et al. "Objective and Comprehensive Evaluation of Bisulfite Short Read Mapping Tools" Adv Bioinformatics. 2014:472045, published Apr. 15, 2014. (Year: 2014).*
EPO, Extended European Search Report for EP Application No. 19933969.8, May 31, 2022.
Liu et al., "Recent Progress and Challenges in High Throughput RNA Methylation Sequencing Data Analysis," Progress in Biochemistry and Biophysics, 2015, vol. 42, No. 10.
Diep, "Library-free methylation sequencing with bisulfite padlock probes," Nature Methods. 2012, vol. 9, No. 3.
CNIPA, First Office Action for CN Application No. 201980092842.5, May 31, 2023.
WIPO, International Search Report for International Application No. PCT/CN2019/092116, Mar. 13, 2020.

* cited by examiner

*Primary Examiner* — Heather Calamita
*Assistant Examiner* — Jessica D Parisi
(74) *Attorney, Agent, or Firm* — Hodgson Russ LLP

(57) ABSTRACT

Provided are a method for constructing a sequencing library based on a DNA sample and use. The method includes: digesting the DNA sample with endonuclease to obtain a DNA sample with single-strand nicks; polymerizing the DNA sample with the single-strand nicks by using polymerase, dATP, dTTP, dGTP, and methylated dCTP to obtain a hybrid DNA, the hybrid DNA including two reversely complementary strands, where a 5'-end of each strand is an original sequence of the DNA sample, a 3'-end of each strand is a synthetic sequence, and all bases C in the 3'-end of each strand are methylated; subjecting the hybrid DNA to bisulfite treatment or other treatment to obtain converted hybrid DNA; and amplifying the converted hybrid DNA to obtain the sequencing library. Thus, the method can be used for whole genome bisulfite sequencing or multiplex PCR targeted sequencing and probe capture sequencing.

8 Claims, 7 Drawing Sheets

Specification includes a Sequence Listing.

SEQUENCE LISTING

```
<160> NUMBER OF SEQ ID NOS: 26

<210> SEQ ID NO 1
<211> LENGTH: 58
<212> TYPE: DNA
<213> ORGANISM: Artificial Sequence
<220> FEATURE:
<223> OTHER INFORMATION: Adapter 1
<220> FEATURE:
<221> NAME/KEY: misc_feature
<222> LOCATION: (1)..(1)
<223> OTHER INFORMATION: phosphorylation
<220> FEATURE:
<221> NAME/KEY: misc_feature
<222> LOCATION: (32)..(41)
<223> OTHER INFORMATION: n is a, c, g, or t

<400> SEQUENCE: 1

agtcggaggc caagcggtct taggaagaca annnnnnnnn ncaactcctt ggctcaca       58


<210> SEQ ID NO 2
<211> LENGTH: 37
<212> TYPE: DNA
<213> ORGANISM: Artificial Sequence
<220> FEATURE:
<223> OTHER INFORMATION: Adapter 2

<400> SEQUENCE: 2

agccaaggtc agtaacgaca tggctacgat ccgactt                              37


<210> SEQ ID NO 3
<211> LENGTH: 17
```

<212> TYPE: DNA
<213> ORGANISM: Artificial Sequence
<220> FEATURE:
<223> OTHER INFORMATION: Universal primer 1
<220> FEATURE:
<221> NAME/KEY: misc_feature
<222> LOCATION: (1)..(1)
<223> OTHER INFORMATION: phosphorylation

<400> SEQUENCE: 3
gaacgacatg gctacga 17

<210> SEQ ID NO 4
<211> LENGTH: 17
<212> TYPE: DNA
<213> ORGANISM: Artificial Sequence
<220> FEATURE:
<223> OTHER INFORMATION: Universal primer 2

<400> SEQUENCE: 4
tgtgagccaa ggagttg 17

<210> SEQ ID NO 5
<211> LENGTH: 25
<212> TYPE: DNA
<213> ORGANISM: Artificial Sequence
<220> FEATURE:
<223> OTHER INFORMATION: Universal primer 3
<220> FEATURE:
<221> NAME/KEY: misc_feature
<222> LOCATION: (1)..(1)
<223> OTHER INFORMATION: phosphorylation

<400> SEQUENCE: 5
gaacgacatg gctacgatcc gactt 25

<210> SEQ ID NO 6
<211> LENGTH: 59
<212> TYPE: DNA
<213> ORGANISM: Artificial Sequence
<220> FEATURE:
<223> OTHER INFORMATION: Universal primer 4
<220> FEATURE:
<221> NAME/KEY: misc_feature
<222> LOCATION: (18)..(27)
<223> OTHER INFORMATION: n is a, c, g, or t

<400> SEQUENCE: 6
tgtgagccaa ggagttgnnn nnnnnnnttg tcttcctaag accgcttggc ctccgactt 59

<210> SEQ ID NO 7
<211> LENGTH: 49
<212> TYPE: DNA
<213> ORGANISM: Artificial Sequence
<220> FEATURE:
<223> OTHER INFORMATION: Specific primer

<400> SEQUENCE: 7
acatggctac gatccgactt gatgtgtttg ggatattgtt tattttatg 49

<210> SEQ ID NO 8
<211> LENGTH: 40
<212> TYPE: DNA
<213> ORGANISM: Artificial Sequence
<220> FEATURE:
<223> OTHER INFORMATION: Specific primer

<400> SEQUENCE: 8
acatggctac gatccgactt tgtgtgttgt ggtgaggagg 40

<210> SEQ ID NO 9
<211> LENGTH: 40
<212> TYPE: DNA
<213> ORGANISM: Artificial Sequence
<220> FEATURE:
<223> OTHER INFORMATION: Specific primer

<400> SEQUENCE: 9
acatggctac gatccgactt aggagggaag gtttgaggtt 40

<210> SEQ ID NO 10
<211> LENGTH: 44
<212> TYPE: DNA
<213> ORGANISM: Artificial Sequence
<220> FEATURE:
<223> OTHER INFORMATION: Specific primer

<400> SEQUENCE: 10
acatggctac gatccgactt ggttagttgg aaggagtgga aatt 44

<210> SEQ ID NO 11
<211> LENGTH: 39
<212> TYPE: DNA
<213> ORGANISM: Artificial Sequence
<220> FEATURE:
<223> OTHER INFORMATION: Specific primer

<400> SEQUENCE: 11
acatggctac gatccgactt acgtgaaagg ggagaggta 39

<210> SEQ ID NO 12
<211> LENGTH: 41
<212> TYPE: DNA
<213> ORGANISM: Artificial Sequence
<220> FEATURE:
<223> OTHER INFORMATION: Specific primer

<400> SEQUENCE: 12
acatggctac gatccgactt ggagtttttt tgtggggtga g 41

<210> SEQ ID NO 13
<211> LENGTH: 42
<212> TYPE: DNA
<213> ORGANISM: Artificial Sequence
<220> FEATURE:
<223> OTHER INFORMATION: Specific primer

<400> SEQUENCE: 13
acatggctac gatccgactt ggtggggtaa aggtgatttt ag 42

<210> SEQ ID NO 14
<211> LENGTH: 47
<212> TYPE: DNA
<213> ORGANISM: Artificial Sequence
<220> FEATURE:
<223> OTHER INFORMATION: Specific primer

<400> SEQUENCE: 14
acatggctac gatccgactt agttttttta gatgttgtga attgggg 47

<210> SEQ ID NO 15
<211> LENGTH: 43
<212> TYPE: DNA
<213> ORGANISM: Artificial Sequence
<220> FEATURE:
<223> OTHER INFORMATION: Specific primer

<400> SEQUENCE: 15
acatggctac gatccgactt tgtggtgtag ttagaagtgg ttt 43

<210> SEQ ID NO 16
<211> LENGTH: 43
<212> TYPE: DNA
<213> ORGANISM: Artificial Sequence
<220> FEATURE:
<223> OTHER INFORMATION: Specific primer

<400> SEQUENCE: 16
acatggctac gatccgactt ggagggttgg taaagtttag aag 43

<210> SEQ ID NO 17
<211> LENGTH: 37
<212> TYPE: DNA
<213> ORGANISM: Artificial Sequence
<220> FEATURE:
<223> OTHER INFORMATION: Specific primer

<400> SEQUENCE: 17
cgcttggcct ccgacttcaa atggcagcag aggaatc 37

<210> SEQ ID NO 18
<211> LENGTH: 36
<212> TYPE: DNA
<213> ORGANISM: Artificial Sequence
<220> FEATURE:
<223> OTHER INFORMATION: Specific primer

<400> SEQUENCE: 18
cgcttggcct ccgacttgaa tggatggctt ggcctg 36

<210> SEQ ID NO 19
<211> LENGTH: 40
<212> TYPE: DNA
<213> ORGANISM: Artificial Sequence
<220> FEATURE:
<223> OTHER INFORMATION: Specific primer

<400> SEQUENCE: 19
cgcttggcct ccgacttgtc ttctagtgga agaagtgaac 40

<210> SEQ ID NO 20
<211> LENGTH: 38
<212> TYPE: DNA
<213> ORGANISM: Artificial Sequence
<220> FEATURE:
<223> OTHER INFORMATION: Specific primer

<400> SEQUENCE: 20
cgcttggcct ccgacttgtc tgacttaaga ctggtggc 38

<210> SEQ ID NO 21
<211> LENGTH: 41
<212> TYPE: DNA
<213> ORGANISM: Artificial Sequence
<220> FEATURE:
<223> OTHER INFORMATION: Specific primer

<400> SEQUENCE: 21
cgcttggcct ccgactttca gtgtacctaa cacaatatag g 41

-continued

```
<210> SEQ ID NO 22
<211> LENGTH: 40
<212> TYPE: DNA
<213> ORGANISM: Artificial Sequence
<220> FEATURE:
<223> OTHER INFORMATION: Specific primer

<400> SEQUENCE: 22

cgcttggcct ccgacttaga cataggtatg acaagttgca                              40


<210> SEQ ID NO 23
<211> LENGTH: 35
<212> TYPE: DNA
<213> ORGANISM: Artificial Sequence
<220> FEATURE:
<223> OTHER INFORMATION: Specific primer

<400> SEQUENCE: 23

cgcttggcct ccgacttcct gatcccaggg tgctg                                   35


<210> SEQ ID NO 24
<211> LENGTH: 37
<212> TYPE: DNA
<213> ORGANISM: Artificial Sequence
<220> FEATURE:
<223> OTHER INFORMATION: Specific primer

<400> SEQUENCE: 24

cgcttggcct ccgacttaga cccagtgaca aaatgcc                                 37


<210> SEQ ID NO 25
<211> LENGTH: 42
<212> TYPE: DNA
<213> ORGANISM: Artificial Sequence
<220> FEATURE:
<223> OTHER INFORMATION: specific primer

<400> SEQUENCE: 25

cgcttggcct ccgacttctt acttaaccat tgtgtccttc cc                           42


<210> SEQ ID NO 26
<211> LENGTH: 40
<212> TYPE: DNA
<213> ORGANISM: Artificial Sequence
<220> FEATURE:
<223> OTHER INFORMATION: Specific primer

<400> SEQUENCE: 26

cgcttggcct ccgacttctc caaagaatga ttcctcattc                              40
```

METHOD AND USE FOR CONSTRUCTION OF SEQUENCING LIBRARY BASED ON DNA SAMPLES

CROSS-REFERENCE TO RELATED APPLICATION

This application is a continuation of International Application No. PCT/CN2019/092116, filed on Jun. 20, 2019, the entire disclosure of which is hereby incorporated by reference.

FIELD

The present disclosure relates to the field of gene sequencing, and particularly, to a method for constructing a sequencing library based on DNA samples and use.

BACKGROUND

DNA methylation, as an apparent regulatory modification, involves in the regulation of protein synthesis without changing the gene sequence. For human beings, DNA methylation is a very intriguing chemical modification. The care of relatives, the body's aging, smoking, excessive drinking, and even obesity will all be truthfully recorded on the genome by methylation. The genome is like a diary, and methylation serves as words to record the experiences of the human body. DNA methylation is an important epigenetic marker information. It is of great significance for the study of epigenetic time-space specificity to obtain the methylation level data of all cytosine sites (C sites) in the whole genome. Base on the next-generation high-throughput sequencing platform, obtaining the DNA methylation profile of the whole genome and analyzing the high-precision methylation modification patterns of specific species will surely have a milestone significance in epigenomics research, and lay a foundation for basic mechanism research with respect to, for example, cell differentiation and tissue development, as well as for the animal and plant breeding, human health and disease research.

However, the whole genome methylation sequencing, i.e., the whole genome bisulfite sequencing (WGBS), as well as the sequencing of specific regions of the genome both face different difficulties.

SUMMARY

The present disclosure aims to at least solve one of the technical problems in the related art to a certain extent. To this end, an object of the present disclosure is to provide a method for constructing a sequencing library based on DNA samples. With this method, the methylated DNA samples can be used to construct the sequencing library, and the obtained sequencing library can satisfy the need for the whole genome methylation sequencing or the methylation sequencing of specific regions.

In the course of long-term research, Applicant has noticed the following issues.

The whole genome methylation sequencing, i.e., the whole genome bisulfite sequencing (WGBS), as one of the most common methods for studying biological methylation, can cover all methylation sites, so as to obtain a comprehensive methylation profile. However, it still encounters many challenges in high-throughput sequencing, which are mainly in the following aspects. First, the unmethylated bases C after bisulfite treatment will be converted into bases U, and the GC content of the whole genome will be extremely changed, resulting in great bias for subsequent amplification. Second, it is very difficult in the analysis of the data after bisulfite treatment, for example, the majority of cytosine (C) in the genome will be converted to thymine (T) after the bisulfite treatment, thereby resulting in base imbalance; due to the limited efficiency in the mapping of the sequencing result to the reference genome, excessive multiple alignments may occur; and the DNA methylation information of some sites cannot be obtained even with an enlarged sequencing coverage, leading to a loss of methylation information of the whole genome.

In general, WGBS is a good method for DNA methylation research. However, considering its defects, detection preference, and problems encountered during bioinformatics analysis, its application is greatly limited. In this regard, Applicant has discovered during the research process that, in the process of library construction and sequencing of DNA-methylated samples, through an improved whole-genome bisulfite sequencing method, the bias for high CG can be reduced and the mapping effectiveness can be increased, thereby ensuring the accurate detection of DNA methylation information. For example, methylated cytosine can be introduced into the DNA template strand by using endonuclease and polymerase, so as to prepare a hybrid DNA strand containing the original template and the newly generated template. The original template in the hybrid DNA strand carries the methylation modification information of the cytosines in the original DNA, while all the cytosines in the newly generated template in the hybrid DNA strand are cytosines that are newly generated and have methylation modification, so that the original information of the DNA can be preserved under the treatment of bisulfite. Under the treatment of bisulfite, the unmethylated cytosine (C) in the original template is converted to uracil (U), and all the cytosines in the newly generated template are methylated, such that a part of the DNA retains DNA methylation information after the bisulfite treatment, and the other part retains the original DNA information. In this way, the hybrid DNA fragments having the preserved DNA methylation information and DNA information can be formed. On basis of these fragments, a sequencing library can be constructed for the whole-genome bisulfite sequencing.

In addition, considering the large data volume and high cost of the whole genome methylation sequencing, the sequence capture technology is adopted to selectively enrich specific regions of the genome, the regions of interest are enriched from the genome by appropriate methods, and then the target regions are sequenced, so that genomics research can be conducted in a targeted way, and the costs can be reduced. With the development of probe capture technology, many companies such as Agilent and Roche have developed the capture products for target region methylation. Agilent adopts the strategy that the target region of interest is first captured, and then the captured region is treated with bisulfite before constructing a library. Such a strategy has the disadvantage that it is impossible to enrich the sample before the capturing, thereby causing a great challenge for the sample of low initial amount. Roche adopts the strategy that bisulfite treatment is first performed, then the sample is enriched, and then probe is designed for capture, and as the designed probe targets the bisulfite-treated DNA, it is necessary to conduct traversal design for the methylated or unmethylated state of cytosines. Thus, the probe design is expensive, and too many variable probes need to be designed, the specificity of the probe capture is also greatly reduced.

In view of the above, by means of the above-mentioned improved method for constructing a whole-genome bisulfite sequencing library, Applicant creatively developed a new capture mode, which combines the advantages of these two capture methods, can enrich DNAs before the capture, and requires fewer types of probes to be designed.

Specifically, the present disclosure provides the following technical solutions.

According to a first aspect of the present disclosure, the present disclosure provides a method for constructing a sequencing library based on a DNA sample. The method includes: digesting the DNA sample with endonuclease to obtain a DNA sample with single-strand nicks; polymerizing the DNA sample with the single-strand nicks by using polymerase, dATP, dTTP, dGTP, and methylated (5-mC) dCTP to obtain a hybrid DNA, the hybrid DNA including two reversely complementary strands, where a 5'-end sequence of each strand is an original sequence of the DNA sample, a 3'-end sequence of each strand is a synthetic sequence, and all bases C in the 3'-end sequence of each strand are methylated; subjecting the hybrid DNA to bisulfite treatment to obtain a converted hybrid DNA; and amplifying the converted hybrid DNA to obtain the sequencing library.

In the present disclosure, the methylated cytosines are introduced into the DNA template strand by using endonuclease and polymerase to prepare a hybrid DNA strand containing the original template and the newly generated template. The original template in the hybrid DNA strand carries the methylation information of the cytosines in the original DNA, and all cytosines in the newly generated template in the hybrid DNA strand are new methylated cytosines, so that the original DNA sequence information can be preserved under the bisulfite treatment. Through the bisulfite treatment, the unmethylated cytosine (C) in the original template can be converted to uracil (U), while the cytosines in the newly generated template are all methylated. Thus, one part of the bisulfite-treated DNA strand retains the DNA methylation information, and the other part retains the original DNA sequence information, thereby forming a hybrid DNA fragment with 5'-end retaining the DNA methylation information and 3'-end retaining original DNA sequence information. Based on these fragments, a sequencing library can be constructed for whole-genome bisulfite sequencing or multiplex PCR targeted sequencing and probe capture sequencing.

Compared with the conventional WGBS library, one part is the base information after methylation, and the other part retains the original DNA base information, which balances the extreme preference of bisulfite during the treatment of the template, and can effectively alleviate the amplification preference of the methylated library on CpG islands in the subsequent PCR process. That is, both the WGBS and WGS libraries can be prepared in one library construction. At the same time, through the retained DNA sequence information, the position information on the genome can be accurately located and mapped, thereby increasing the accuracy of methylation mapping; and the operation steps are simplified, and the process of library interruption, end repair and A-tailing can be completed in one step. In addition, multiplex PCR capture technology can be developed based on the hybrid strand library. One PCR primer of the capture technology is designed to be located on the DNA sequence that retains the methylation information, and another PCR primer is designed to be located on the DNA sequence that retains the original DNA sequence information, thereby avoiding the presence of primer dimers in the design of methylation primers for the converted DNA in the conventional art, and providing higher specificity than conventional methylation primers. Moreover, based on the hybrid library, a probe based capture technology can be developed, and the probe is designed to be located on the sequence that retains the original DNA sequence information. Compared with design for the converted DNA sequence, the difficulty of probe design is greatly reduced.

According to the embodiments of the present disclosure, the above-mentioned method for constructing a sequencing library based on a DNA sample may further include the following technical features.

In some embodiments of the present disclosure, the endonuclease is at least one of Dnase I or Dnase II, or the endonuclease is any endonuclease capable of producing the single-strand nicks. In some embodiments of the present disclosure, the polymerase is BST polymerase, phi29 polymerase, klenow polymerase, or any polymerase capable of polymerizing DNA.

In some embodiments of the present disclosure, the DNA sample with the single-strand nicks has a length of 100 bp to 1000 bp.

In some embodiments of the present disclosure, the method further includes: ligating a methylation sequencing adapter to the hybrid DNA, and performing bisulfate treatment, bisulfite treatment or other treatment capable of converting methylation information, to obtain the converted hybrid DNA, where the methylation sequencing adapter includes a first universal sequence and a second universal sequence; and amplifying the converted hybrid DNA by using universal primers to obtain a sequencing library, where the universal primers matches the first universal sequence and the second universal sequence. The 5'-end of the converted hybrid DNA strand is a converted DNA sequence, in which all the unmethylated cytosines are converted into U bases; the 3'-end of the converted hybrid DNA strand is the newly synthesized DNA sequence, in which all the cytosines are methylated and the original DNA sequence information is preserved unchanged under the conversion treatment. By constructing the sequencing library in this way, the whole genome bisulfite sequencing can be achieved.

In some embodiments of the present disclosure, the methylation sequencing adapter is suitable for any one of MGI, Illumina, Proton, or other sequencing platform.

In some embodiments of the present disclosure, the DNA sample is a whole genome DNA sample.

In some embodiments of the present disclosure, the method further includes: directly subjecting the hybrid DNA that are not ligated with adapters to the bisulfate treatment, bisulfite treatment, or other treatments capable of transforming methylation information, so as to obtain the converted hybrid DNA, where the 5'-end of each converted hybrid DNA strand is a converted DNA sequence, in which all the unmethylated cytosines are converted into U bases, and the 3'-end of the converted hybrid DNA strand is a newly synthesized DNA sequence, in which all the cytosines are methylated and the original DNA sequence information is preserved unchanged under the conversion treatment; and then amplifying the converted hybrid DNA by using specific primers to obtain the target region sequencing library of the DNA sample. The specific primers include first specific primer and second specific primers, a sequence of the first specific primer is the same as with the 5'-end sequence of the converted hybrid DNA, and a sequence of the second specific primer is complementary to the 3'-end sequence of the converted hybrid DNA.

Corresponding primers, i.e., the first specific primer and the second specific primer, are designed for the 5'-end and the 3'-end of any strand of the converted hybrid DNA, respectively. One specific primer is designed for the DNA sequence that retains the methylation information, and the other specific primer is designed for the original DNA sequence. One primer is rich in ATG, and the other primer contains ATCG, so as to reduce the primer dimers formed in the process of methylation multiplex PCR.

In some embodiments of the present disclosure, the method further includes: hybrid capturing the converted hybrid DNA by using a probe and eluting to obtain a hybridized product, where the probe is configured to hybridize a 3'-end sequence of the converted hybrid DNA, i.e., the template strand whose DNA sequence information remains unchanged after the bisulfate treatment; and amplifying the hybridized product to obtain the sequencing library. According to the method of the present disclosure, in the process of hybrid capture with the probe, the probe is designed for the strand that maintains the original DNA sequence information, thereby reducing the difficulty in designing the capture probe, enhancing the specificity of the capture probe, and greatly increasing the capture efficiency and data utilization, when compared with ordinary capture methods in which probe is designed for the converted DNA strand. Moreover, the method of the present disclosure is suitable for the construction and sequencing of methylation targeted libraries of trace DNA.

According to a second aspect of the present disclosure, the present disclosure provides a method for sequencing a DNA sample. The method includes: constructing a sequencing library based on the DNA sample by the method described in any one of the embodiments of the first aspect of the present disclosure; and sequencing the sequencing library to obtain sequencing results of the DNA sample.

According to an embodiment of the present disclosure, the sequencing is paired-end sequencing or single-end sequencing.

According to a third aspect of the present disclosure, the present disclosure provides a method for determining a methylation state of a DNA sample. The method includes: constructing a sequencing library based on the DNA sample by the method described in any one of the embodiments of the first aspect of the present disclosure; sequencing the sequencing library to obtain sequencing results of the DNA sample; aligning the sequencing results of a 5'-end and a 3'-end of the DNA sample respectively with a reference genome to determine position information of the 5'-end and the 3'-end; and analyzing a position of the DNA sample by comparison based on the position information of the 5'-end and the 3'-end to determine the methylation state of the DNA sample.

According to an embodiment of the present disclosure, the above-mentioned method for determining the methylation state of the DNA sample may further include the following technical features.

In some embodiments of the present disclosure, the step of aligning the sequencing results of a 5'-end and a 3'-end of the DNA sample respectively with a reference genome to determine position information of the 5'-end and the 3'-end includes: when the 3'-end corresponds to multiple candidate positions, the 5'-end corresponds to one candidate position, and a position adjacent to the candidate position corresponding to the 5'-end is one of the multiple candidate positions corresponding to the 3'-end, determining the position information of the 5'-end and the 3'-end based on the candidate position corresponding to the 5'-end as being usable; when the 3'-end corresponds to multiple candidate positions, the 5'-end corresponds to multiple candidate positions, determining the position information of the 5'-end and the 3'-end based on a common optimal candidate position of the 5'-end and the 3'-end; when the 3'-end corresponds to one candidate position, the 5'-end corresponds to multiple candidate positions, and a position adjacent to the candidate position corresponding to the 3'-end is one of the multiple candidate positions corresponding to the 5'-end, determining the position information of the 5'-end and the 3'-end based on the candidate position corresponding to the 3'-end as being usable; when the 3'-end corresponds to one candidate position, the 5'-end corresponds to one candidate position, and a position adjacent to the candidate position corresponding to the 3'-end is adjacent to the candidate position of the 5'-end, determining the position information of the 5'-end and the 3'-end based on the candidate position corresponding to the 3'-end or the candidate position corresponding to the 5'-end. Other cases belong to multiplex mapping, and the mapping position of reads cannot be accurately determined, but the position to which the 3'-end is mapped can be determined as the main mapping position.

In some embodiments of the present disclosure, the 3'-end is aligned with the reference genome using BWA software, and the 5'-end is aligned with the reference genome using BS-map software.

According to a fourth aspect of the present disclosure, the present disclosure provides a kit, which includes an endonuclease, a nucleic acid amplification reagent, a methylated dCTP, and a methylation detection reagent.

In some embodiments of the present disclosure, the kit further includes first specific primers and second specific primers. The first specific primers include primers set forth as SEQ ID NO: 7 to SEQ ID NO: 16, and the second specific primers include primers set forth as SEQ ID NO: 17 to SEQ ID NO: 26.

In some embodiments of the present disclosure, the kit further includes a probe configured to capture a target sequence and construct a target region nucleic acid library.

According to a fifth aspect of the present disclosure, the present disclosure provides a double-stranded DNA including two reversely complementary strands, in which each strand includes a 5'-end sequence and a 3'-end sequence, and all bases C in the 3'-end sequence of each strand are methylated. The 5'-end sequence of each strand DNA is a sequence retaining methylation information, a sequence in which all the unmethylated cytosines can be converted into bases U through the bisulfate treatment, or a sequence obtained through other enzyme treatments (e.g., first TET2 oxidation treatment, and then APOBEC enzyme treatment), in which all bases C of the 3'-end sequence are methylated, and preserve the cytosine information unchanged during the conversion process.

In some embodiments of the present disclosure, the double-stranded DNA has a length of 100 bp to 1000 bp.

BRIEF DESCRIPTION OF DRAWINGS

The above and/or additional aspects and advantages of the present disclosure will become apparent and easy to understand from the description of the embodiments in conjunction with the following drawings, in which.

DESCRIPTION OF EMBODIMENTS

Figure 1:
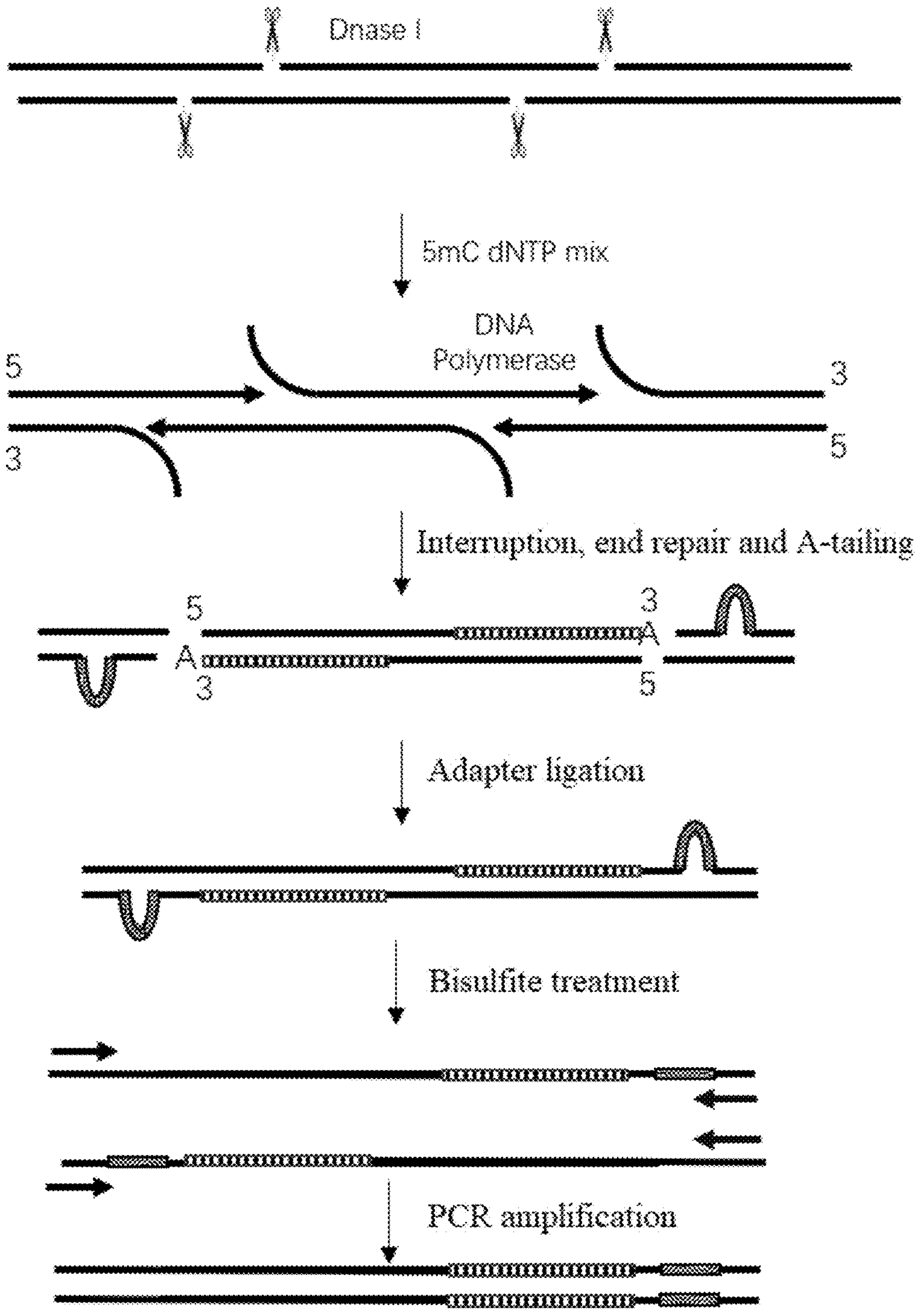
FIG. 1 is a flowchart of a DNA methylation hybrid library construction according to an embodiment of the present disclosure.
Figure 2:
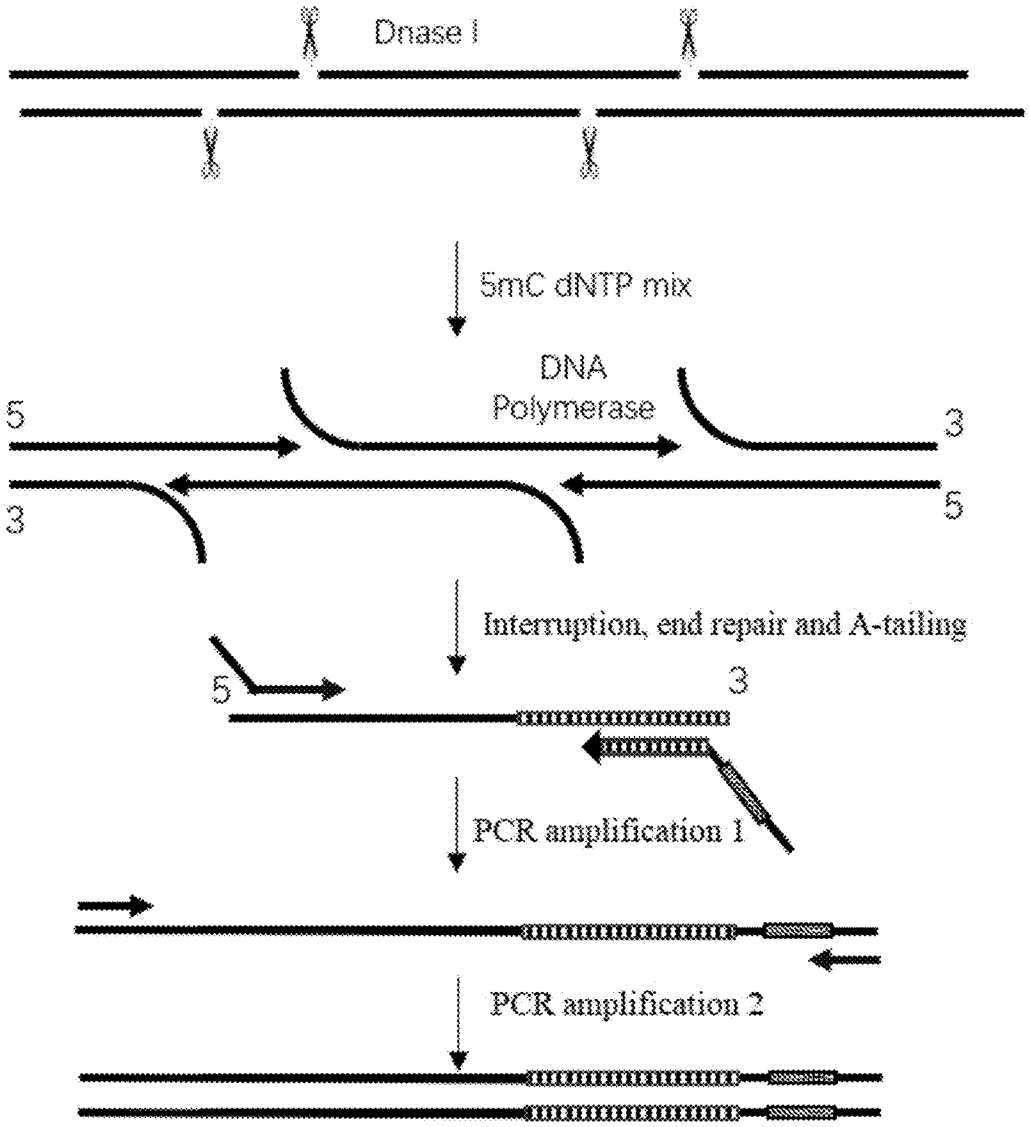
FIG. 2 is a flowchart of a DNA methylation hybrid multiplex PCR according to an embodiment of the present disclosure.

The embodiments of the present disclosure are described in detail below. Examples of the embodiments are shown in the accompanying drawings, throughout which the same or similar reference numerals indicate the same or similar elements or elements with the same or similar functions. The embodiments described below with reference to the accompanying drawings are exemplary, and are intended to explain the present disclosure, but should not be construed as limiting the present disclosure.

In order to have a more intuitive understanding of the present disclosure, the terms present in the present disclosure are explained and described below. Those skilled in the art shall understand that these explanations and descriptions are only for more convenient understanding and should not be regarded as limiting the protection scope of the present disclosure.

Herein, unless otherwise specified, in order to specify a base, the base N or base n can be base A, T, C, or G.

Herein, with respect to the description of the conversion treatment using bisulfite, both bisulfate and bisulfite have the same meaning, and the conversion treatment using other enzymes shall also be included in the scope of the present disclosure.

According to one aspect of the present disclosure, the present disclosure provides a method for constructing a sequencing library based on a DNA sample, including: (1) digesting the DNA sample with endonuclease to obtain the DNA sample with single-strand nicks; (2) polymerizing the DNA sample with the single-strand nicks by using polymerase, dATP, dTTP, dGTP, and methylated dCTP to obtain a hybrid DNA, where a 5'-end of each strand of the hybrid DNA is an original sequence of the DNA sample, a 3'-end of each strand of the hybrid DNA is a synthetic sequence, and all the bases C in the 3'-end of each strand of the hybrid DNA are methylated; (3) subjecting the hybrid DNA to bisulfite treatment to obtain converted hybrid DNA; and (4) amplifying the converted hybrid DNA to obtain the sequencing library.

The single-strand nicks are randomly formed on the DNA sample after being digested with an endonuclease, e.g., Dnase I, and at the single-strand nicks, the 5'-end is phosphorylated and the 3'-end carries hydroxyl group. By adding a mixture of polymerase (e.g., BST polymerase) together with the methylated dCTP and the normal dATP, dTTP, and dGTP in an equivalent molar ratio, the polymerization is initiated by the BST polymerase from the 3'-end of the nick, and the nicked strand is replaced to produce the hybrid DNA fragment including the original DNA and the newly generated DNA. The original DNA retains the original methylation information, the bases C on the newly generated DNA are all methylated, and the newly generated DNA preserves the original DNA information under the treatment of bisulfite or enzymes.

The DNA sample may be a genomic DNA. In addition to Dnase I, the suitable endonucleases can also be any other restriction endonucleases capable of producing the single-strand nicks such as Dnase II, or the like, or other endonucleases capable of producing the single-strand nicks. The length of the DNA sample can be controlled between 100 bp and 1000 bp.

The polymerase and 5-mC dNTPs (an equimolar mixture of 5 m dCTP, dATP, dTTP, and dGTP) are used for polymerization and replacement reaction, and the A-tailing is added to the 3'-ends of double strands of the newly generated DNA. In addition to the BST polymerase, the suitable polymerase can also be a polymerases with displacement activity, such as phi29, or the polymerase with 5-3 exonuclease activity and A-tailing activity at the ends, such as klenow, etc., or any other DNA polymerases with or without A-tailing activity and with replacement or 5-3 exonuclease activity.

After the DNA sample is processed through the above steps (1) and (2), the cytosines at the 5'-end of the DNA strands in the obtained hybrid DNA retain the original methylation modification information, and all the cytosines at the 3'-end of the DNA strands in the obtained hybrid DNA are methylated cytosines after the conversion. Methylation sequencing adapters are connected to the hybrid DNA. Then, under the bisulfite treatment, the unmethylated bases C at the 5'-end of the hybrid DNA are converted into bases U, and the methylated bases C at the 5'-end of the hybrid DNA remain unchanged and retain the original methylation information; all the methylated bases C at the 3'-end of the DNA strand remain unchanged and retain the original DNA sequence information. Through the universal primer on the methylation sequencing adapter, the PCR amplification is performed to obtain a sequencing library that retains DNA methylation information and original DNA sequence information, and the obtained library can be subjected to high-throughput sequencing to obtain DNA methylation information and original DNA sequence information. In at least some embodiments, the respective methylation sequencing adapters can be any methylation sequencing adapters of MGI, Illumina, Proton, or other sequencing platforms. Accordingly, these platforms can be used to perform high-throughput sequencing on the obtained sequencing library.

In at least some embodiments, the high-throughput sequencing can be paired-end sequencing or single-end sequencing, preferably paired-end sequencing, one read of which contains a bisulfite-treated information sites: unmethylated cytosines have been converted into thymines, and this one read is used for determining the methylated sites; and the other read of which retains the original DNA information, and is used to assist in positioning the mapping information. In this way, the genomic methylation information and the genomic DNA sequence information can be accurately obtained at the same time.

The nucleic acid sequence analysis and mapping method is paired-end analysis. The read containing the bisulfite-treated information sites is mapped to the whole genome information by using software such as BS-map (methylation mapping method) to obtain position information thereof on the genome, and the read retaining the original sequence information is mapped to the whole genome information by using BWA software or the like to obtain position information thereof on the genome. 1) If the former one corresponds to multiple positions on the genome information, the latter one corresponds one position, and a position adjacent to the latter one (within 100 bp to 1000 bp) is a candidate position of the former one, then the position of the latter one is used. 2) If the former one corresponds multiple positions and the latter one corresponds multiple positions, a position that is shared by both and is not far apart is used; and if there are multiple such positions, the optimal mapping position is used. 3) If the former one corresponds one position, the latter one corresponds multiple positions, and a position adjacent to the former one (within 100 bp to 1000 bp) is a candidate position of the latter one, then the position of the former is used. The best mapping results are selected, redundancy the sequences generated by PCR is eliminated, the genome information and the genomic methylation information are analyzed, and the genomic base mutation frequency and the genomic methylation rate are statistically analyzed.

In at least some embodiments, before performing step (4), one or more pairs of PCR amplification primers for amplifying the gene locus of interest are designed, one primer is positioned in a region that retains DNA methylation information, the other primer is positioned in a region that retains the original DNA information, and the PCR amplification is performed to obtain a sequence of the gene locus of interest and methylation analysis is performed. The amplified product can be used for electrophoresis, Sanger's sequencing, or high-throughput sequencing, etc. One primer is designed to be positioned at the sequence where cytosines are methylated, and the other primer is positioned at the sequence where the unmethylated cytosines are converted into thymines, and then PCR amplification is performed to obtain the sequence of the gene locus of interest and perform methylation analysis.

In at least some embodiments, before performing step (4), the preserved original DNA sequence near the methylation site of interest is hybridized with a probe, and after the entire DNA molecular strand is captured, a target site methylation library can be obtained. Through magnetic bead adsorption and elution, a target site methylation capture library can be obtained, which is then subjected to PCR amplification to obtain a library for high-throughput sequencing. By designing probes, it is possible to enrich and amplify the bisulfate-treated DNA, and increase the amount of capture input, and it is unnecessary to traverse all methylation states for probe design, which is beneficial to reduce the types of probes to be designed and improve the specificity of the probe capture.

The probe can be designed as a DNA probe or an RNA probe, a liquid phase or solid phase probe. The probe can have a length ranging from 60 nt to 120 nt. The probe is designed for the original DNA sequence, and the probe contains biotin or other modifications for the subsequent separation and purification, or the probe is designed by other methods that are compatible with all types of existing probes for DNA sequence capture. The bisulfate-treated template with a half retaining the DNA methylation information and a half retaining the DNA sequence information is captured by hybridizing with the probes, and the DNA probe is bonded to the DNA portion retaining the DNA sequence information (preferably obtained from the above scheme). The DNA obtained after hybridization is captured by streptavidin-modified magnetic beads or other biologically modified magnetic beads and eluted, and the eluted product is subjected to PCR amplification to obtain a sequencing library for sequencing.

The solutions of the present disclosure will be explained below in conjunction with examples. Those skilled in the art will understand that the following examples are only used to illustrate the present disclosure and should not be regarded as limiting the scope of the present disclosure. Where specific techniques or conditions are not indicated in the examples, the procedures shall be carried out in accordance with the techniques or conditions described in the literature in the art or in accordance with the product specification. The reagents or instruments used without indication of the manufacturers are all conventional products that can be purchased commercially.

Example 1: Whole Genome Methylation Library Construction and Sequencing 10 ng of gDNA from Yanhuang cell line was taken for a methylation whole genome library construction according to the method of the present disclosure and the conventional method. The library was sequenced on the BGISEQ-500 sequencer, with a sequencing type PE100, and a sequencing depth of 30×, and then data analysis was conducted, including analysis of data utilization, mapping ratio, GC bias and other performance. The experimental process is as follows:

1. Interruption, End Repair and A-tailing

The product was subjected to end repair and A-tailing reaction using NEB's Dnase I (Cat. No. 0303S) and BST (Cat. No. M0374S) polymerases. The reaction system and conditions are as follows:

| | |
|---|---|
| DNA | 37 μL |
| NEB buffer | 10 μL |
| Dnase I (0.4 U/μL) | 1 μL |
| BST polymerase | 1 μL |
| 5-mC dNTP mix (10 mM) | 1 μL |
| Total volume | 50 μL |

The above reaction system was placed on a PCR instrument, 37° C. for 10 minutes and 65° C. for 30 minutes. 5-mC dNTP mix represents a mixture of methylated dCTP and normal dATP, dTTP, and dGTP.

After the reaction was finished, purification was performed with 1.0× AMPure magnetic beads, and finally the purified product was dissolved in 20 μl of elution buffer.

2. Ligation of Methylation Adapters:

1) A ligation reaction system of the methylation adapters (also referred as to "methylation sequencing adapter") was prepared for the DNA obtained in the previous step according to the following table:

| | |
|---|---|
| DNA | 18 μL |
| 2 × Rapid ligation buffer (L603-HC-L Enzymatic Enzymatic) | 25 μL |
| Methylation sequencing adapter (100 uM)* (Baosheng biosynthesis) | 4 μL |
| T4 DNA ligase (Rapid, L603-HC-L Enzymatic) | 3 μL |
| Total volume | 50 μL |

In the above table, sequence of the *methylation adapter are as below:

```
Adapter 1 (SEQ ID NO: 1):
5'-/5Phos/AGTCGGAGGCCAAGCGGTCTTAGGAAGACAANNNNNNNNNN

NGGCTCACA-3;

Adapter 2 (SEQ ID NO: 2):
5' AGCCAAGGTCAGTAACGACATGGCTACGATCCGACTT.
```

Cytosines in the sequences of Adapter 1 and Adapter 2 were all protected with methylation modification, and the bases N are a sample index sequence.

2) The above reaction system was placed on a Thermomixer (Eppendorf) at 20° C. and reacted for 15 minutes to obtain a ligation product. After the reaction was finished, the product was purified by using 1.0× AMPure magnetic beads, and the purified product was dissolved in 22 μl of elution buffer.

3. Bisulfite Treatment

The above-mentioned ligated DNA was subjected to bisulfate co-treatment using the EZ DNA Methylation-Gold Kit™ (ZYMO). The specific steps are as follows:

(1) Reagents

Preparation of CT conversion reagent solution: the CT conversion reagent (solid mixture) was taken out from the kit, added with 900 μL of water, 50 μL of M-dissolving buffer, and 300 μL of M-Dilution Buffer, dissolved at room temperature and oscillated for 10 minutes or shaken on a shaker for 10 minutes.

Preparation of M-washing buffer: 24 mL of 100% ethanol was added to the M-washing buffer for later use.

(2) 130 μL of CT conversion reagent solution and the above-mentioned ligated DNA were added to the PCR tube, and the mixed sample was suspended by flicking or pipetting.

The sample tube was placed on the PCR instrument to perform the following steps: 98° C. for 5 minutes, and 64° C. for 2.5 hours.

After the above operations were finished, the sample immediately proceeded to the next operation or was stored at 4° C. (up to 20 hours) for later use.

(3) The Zymo-Spin IC™ Column was placed into the Collection Tube, and 600 μL of M-binding buffer was added.

The above bisulfate-treated sample was added to the Zymo-Spin IC™ Column containing the M-binding buffer, and the lid was closed and mixed evenly upside down.

Centrifugation was performed at full speed (>10,000×g) for 30 seconds, and the collected solution in the collection tube was discarded.

100 μL of M-washing buffer was added to the column, followed by centrifugation at full speed (>10,000×g) for 30 seconds, and discarding the liquid in the collection tube.

200 μL of M-desulphonation buffer was added to the column and stood still at room temperature for 15 minutes, followed by centrifugation at full speed (>10,000×g) for 30 seconds, and discarding the liquid in the collection tube.

200 μL of M-washing buffer was added to the column, followed by centrifugation at full speed (>10,000×g) for 30 s, discarding the liquid in the collection tube; and this step was repeated one more time.

The Zymo-Spin IC™ Column was placed in a new EP tube (1.5 mL), followed by adding 20 μL of M-elution buffer r to the column matrix, standing still at room temperature for 2 minutes, centrifugation at full speed (>10,000×g), and eluting the target fragment DNA.

4. PCR Amplification

According to the following system, a PCR reaction system was prepared with the target fragment DNA obtained in the previous step, and the amplification enzyme system was KAPA HiFi Hot Start Uracil+ReadyMix (2×) (from KAPA Biosystems, Cat. No. kk2801).

| | |
|---|---|
| Ligated DNA from the previous step | 20 μL |
| 2 × kapa HIFI hot start Uracil ready mix | 25 μL |
| Universal primer 1 (10 μM) | 2.5 μL |
| Universal primer 2 (10 μM) | 2.5 μL |
| Total volume | 50 μL |

```
Universal primer 1 (SEQ ID NO: 3):
/5Phos/GAACGACATGGCTACGA

Universal primer 2 (SEQ ID NO: 4):
TGTGAGCCAAGGAGTTG
```

PCR Reaction Conditions:

| | | |
|---|---|---|
| 94° C. | 1 min | |
| 94° C. | 30 s | |
| 55° C. | 30 s | 12 cycles |
| 72° C. | 30 s | |
| 72° C. | 5 min | |
| 12° C. | maintained | |

After the reaction was finished, purification was performed with AMPure magnetic beads, and the purified product was dissolved in 22 μl of elution buffer.

5. Library Detection

The size and content of the insert fragments of the library were analyzed using the Bioanalyzer analysis system (Agilent, Santa Clara, USA). According, the constructed high-throughput sequencing library of the specific genome region of the sample was detected.

6. Sequencing

The obtained library was subjected to high-throughput sequencing on the sequencing platform BGIseq-500, sequencing type PE100, and the sequencing data was subjected to alignment to statistically analyze various basic parameters, including sequencing data, usable data, and mapping data, etc. The results are listed in Table 1 below.

Figure 3:
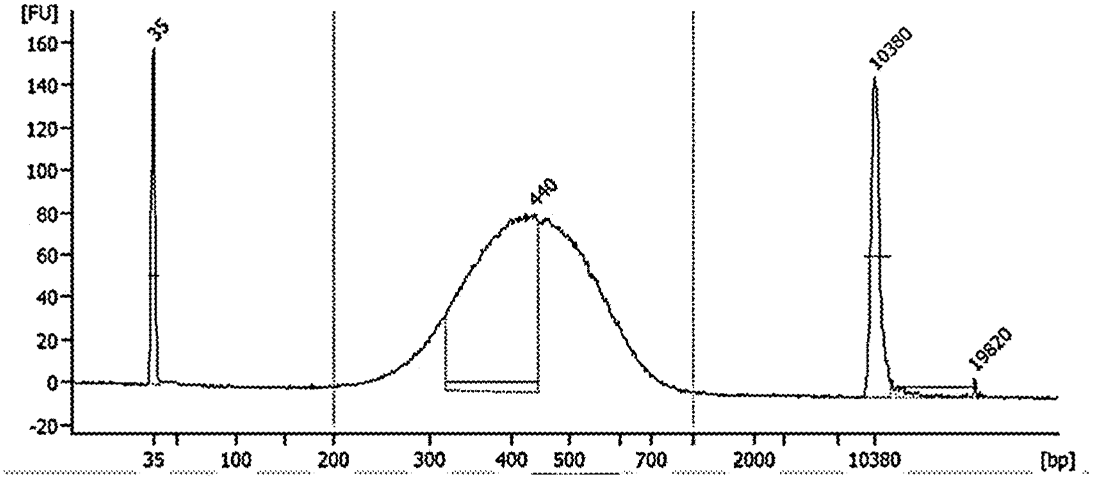
FIG. 3 is a diagram of quality inspection results of a methylated DNA hybrid library provided according to an embodiment of the present disclosure.

FIG. 3 illustrates the library quality inspection map obtained by the method of the present disclosure.

TABLE 1

| Sequencing results | | | | | |
|---|---|---|---|---|---|
| | Sequencing data | Mapping data | Covered CpG | Coverage | 10 × coverage |
| Method of the present disclosure | 13212652122 | 125916574726 | 42698531 | 98.30% | 91.20% |
| Traditional WGBS | 12865253665 | 90314080729 | 36578961 | 94.50% | 81.30% |

Figure 4:
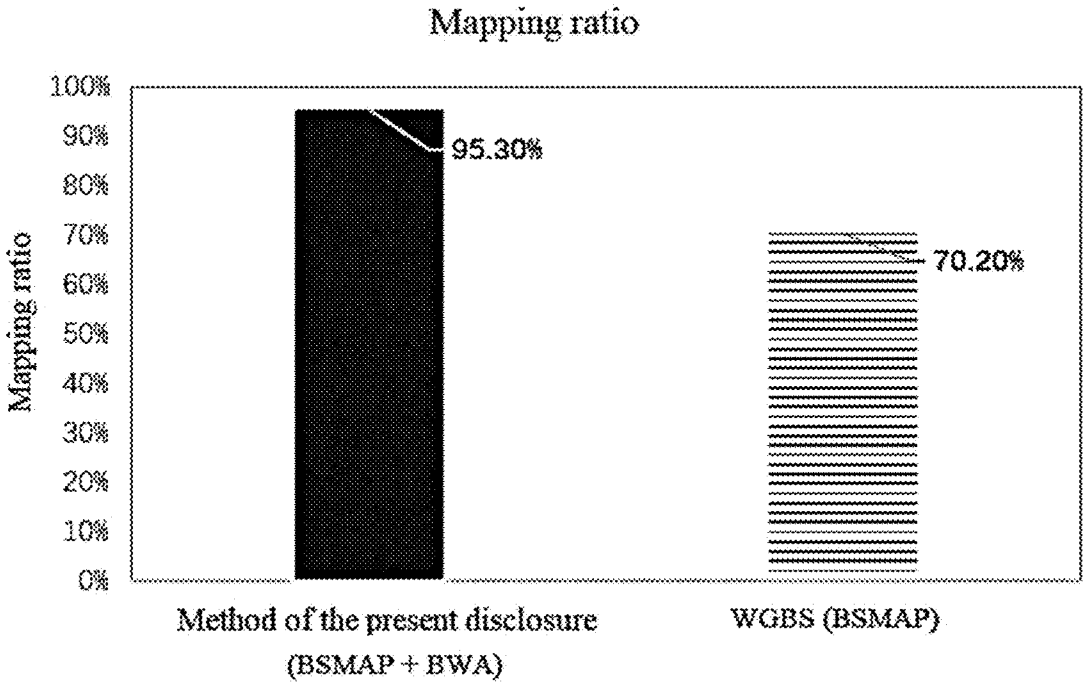
FIG. 4 is a graph of mapping ratio results of different methods provided according to an embodiment of the present disclosure.

In Table 1, the covered CpG refers to the number of CpG sites with a depth of 1× or more, the coverage refers to a ratio of CpG sites with a depth of 1× or more to all CpG sites, and the 10× coverage refers to a ratio of CpG sites with depths of 10× or more to all CpG sites. The obtained results of the mapping ratio by the above methods are illustrated in FIG. 4. It can be seen from the results that the mapping ratio obtained by the method of the present disclosure is superior to that obtained by the conventional WGBS.

Figure 5:
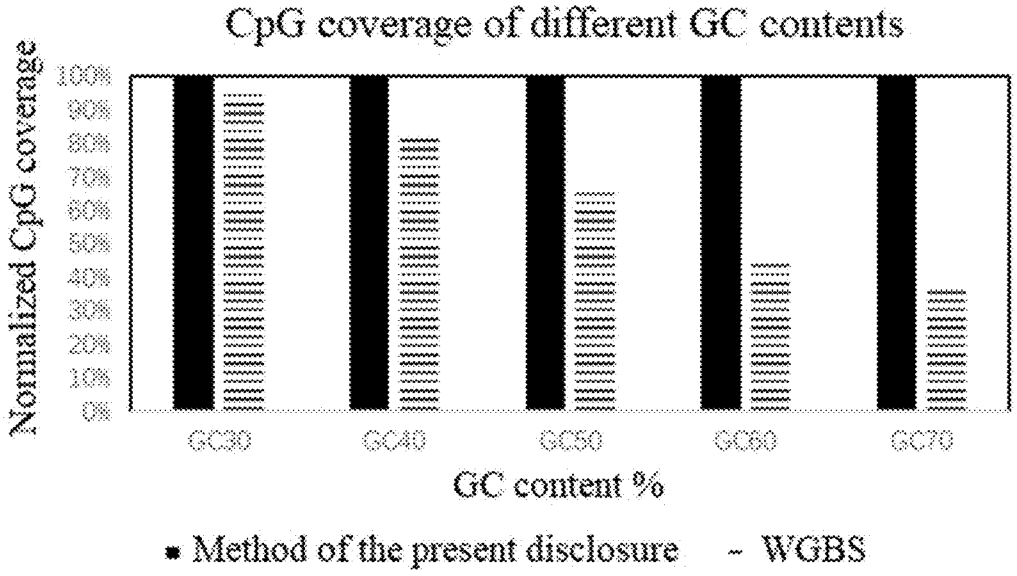
FIG. 5 is a graph showing coverage results of CpG sites on regions of different GC contents by different methods according to an embodiment of the present disclosure.

The coverages of the GC content obtained by using different methods are shown in FIG. 5. From the results, it can be seen that the coverage of the GC content obtained by the method of the present disclosure is superior to that obtained by the conventional WGBS.

Figure 6:
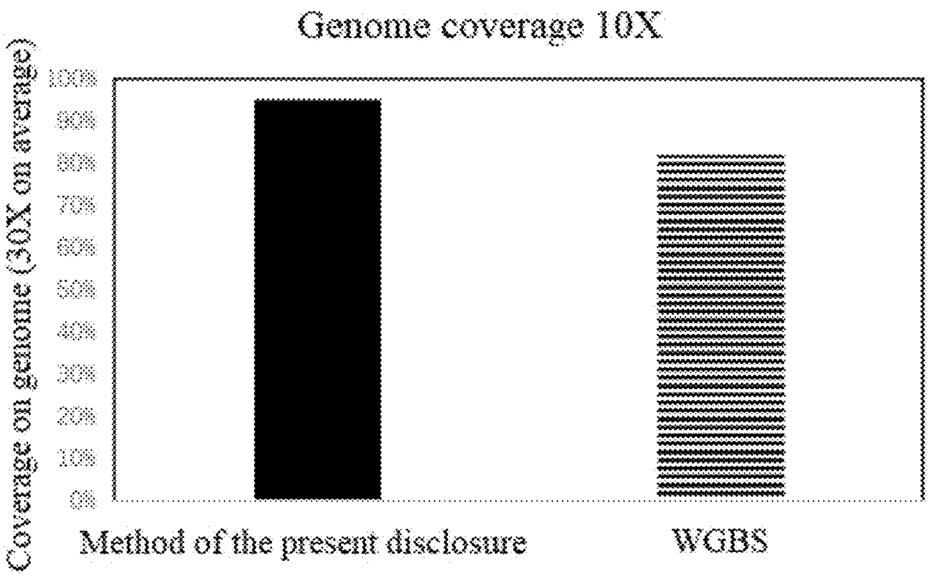
FIG. 6 illustrates coverage results on the whole genome by different methods according to an embodiment of the present disclosure.

The results of the coverage on the whole genome obtained by different methods are shown in FIG. 6. From the results, it can be seen that the coverage on the whole genome obtained by the method of the present disclosure is superior to that obtained by the conventional method.

Moreover, from the results shown in Table 1, it can be seen that the number of CpG sites detected by the method of the present disclosure is higher than that by the conventional WGBS.

Example 2: Targeted Methylation Library Construction

Primers were designed for 10 methylated sites. Forward primers was designed to be located upstream of the sites; for the bisulfite-treated genome sequence, the reverse primers were designed to be located downstream of the sites; and for the original genome sequence (sequence as indicated in Table 1), and the methylated DNA mixture after bisulfite treatment was subjected to multiplex PCR using the multiplex primers.

1. Interruption, End Repair and A-Tailing

The product was subjected to end repair and A-tailing reaction using NEB's Dnase I and BST. The reaction system and conditions are as follows.

| | |
|---|---|
| DNA | 37 μL |
| NEB buffer | 10 μL |
| Dnase I (0.4 U/μL) | 1 μL |
| BST | 1 μL |
| 5-mC dNTP mix (10 mM) | 1 μL |
| Total volume | 50 μL |

The above reaction system was placed on a PCR instrument, 37° C. for 10 minutes, and 65° C. for 10 minutes. After the reaction, purification was performed with 1.0× AMPure magnetic beads, and the purified product was dissolved in 20 μl of elution buffer.

2. Bisulfite Treatment

The above ligated DNA was subjected to bisulfite co-treatment using the EZ DNA Methylation-Gold Kit™ (ZYMO). The specific steps are described as below.

1) Preparation of CT conversion reagent solution: the CT conversion reagent (solid mixture) was taken out from the kit, added with 900 μL of water, 50 μL of M-dissolving buffer, and 300 μL of M-dilution buffer, dissolved at room temperature, and oscillated for 10 minutes or shaken on a shaker for 10 minutes.

Preparation of M-washing buffer: 24 mL of 100% ethanol was added to the M-washing buffer for later use.

2) 130 μL of CT conversion reagent solution and the above ligated DNA were added to the PCR tube, and the mixed sample was suspended by flicking or pipetting.

Then, the sample tube was placed on the PCR instrument to perform the following steps: 98° C. for 5 minutes; and 64° C. for 2.5 hours;

After the above operations were finished, the sample immediately proceeded to the next step or was stored at 4° C. (up to 20 hours) for later use.

3) The Zymo-Spin IC™ Column was placed into the collection tube, and 600 μL of M-binding buffer was added.

The bisulfite-treated sample was added to the Zymo-Spin IC™ Column containing the M-binding buffer, and the column was covered with the lid and mixed evenly upside down.

Centrifugation was performed at full speed (>10,000×g) for 30 seconds, and the collection solution in the collection tube was discarded.

100 μL of M-washing buffer was added to the column, followed by centrifugation at full speed (>10,000×g) for 30 seconds, and discarding the liquid in the collection tube.

200 μL of M-desulphonation buffer was added to the column and stood still at room temperature for 15 minutes, followed by centrifugation at full speed (>10,000×g) for 30 seconds, and discarding the liquid in the collection tube.

200 μL of M-washing buffer was added to the column, followed by centrifugation at full speed (>10,000×g) for 30 s, discarding the liquid in the collection tube, and repeating this step one more time.

The Zymo-Spin IC™ Column was placed in a new EP tube (1.5 mL), followed by adding 20 μL of M-elution buffer r to the column matrix, standing still at room temperature for 2 minutes, centrifugation at full speed (>10,000×g), and eluting the target fragment DNA.

3. First Round of PCR Amplification

According to the following system, a PCR reaction system was prepared with the target fragment DNAs obtained in the previous step:

| | |
|---|---|
| Treated DNA from the previous step | 20 μL |
| 2 × kapa HIFI hot start Uracil ready mix | 25 μL |
| Specific primer pool 1 (10 μM, Table 3) | 5 μL |
| Total volume | 50 μL |

PCR reaction conditions:

| | | |
|---|---|---|
| 94° C. | 1 min | |
| 94° C. | 30 s | |
| 58° C. | 2 min | 15 cycles |
| 72° C. | 30 s | |
| 72° C. | 5 min | |
| 12° C. | maintained | |

After the reaction was finished, purification was performed with 1.0X AMPure magnetic beads, and the purified product was dissolved in 22 μl of elution buffer.

4. Second Round of PCR Amplification

According to the following system, a PCR reaction system was prepared with the target fragment DNAs obtained in the previous step:

| | |
|---|---|
| Treated DNA from previous step | 20 μL |
| 2 × kapa HIFI hot start Uracil ready mix | 25 μL |
| Universal primer 3 | 2.5 μL |
| Universal primer 4 | 2.5 μL |
| Total volume | 50 μL |

```
Universal primer 3 (SEQ ID NO: 5):
/5Phos/GAACGACATGGCTACGATCCGACTT;

Universal primer 4 (SEQ ID NO: 6):
TGTGAGCCAAGGAGTTGNNNNNNNNNNTTGTCTTCCTAAGACCGCTTGGC

CTCCGACTT
```

Bases N are a molecular index.

PCR reaction conditions are as follows.

| | | |
|---|---|---|
| 94° C. | 1 min | |
| 94° C. | 30 s | |
| 58° C. | 2 min | 15 cycles |
| 72° C. | 30 s | |
| 72° C. | 5 min | |
| 12° C. | maintained | |

After the reaction was completed, purification was performed with 1.0×AMPure magnetic beads, and the purified product was dissolved in 22 μl of elution buffer.

5. Library Detection

The size and content of the insert fragments of the library were analyzed using the Bioanalyzer analysis system (Agilent, Santa Clara, USA). According, the constructed high-throughput sequencing library of specific regions of the genome of the sample was detected.

6. Sequencing

The obtained library was subjected to high-throughput sequencing on sequencing platform BGIseq-500, with sequencing type PE100, and the sequencing data was subjected to alignment to statistically analyze various basic parameters, including sequencing data, usable data, mapping ratio, GC content, etc.

Figure 7:
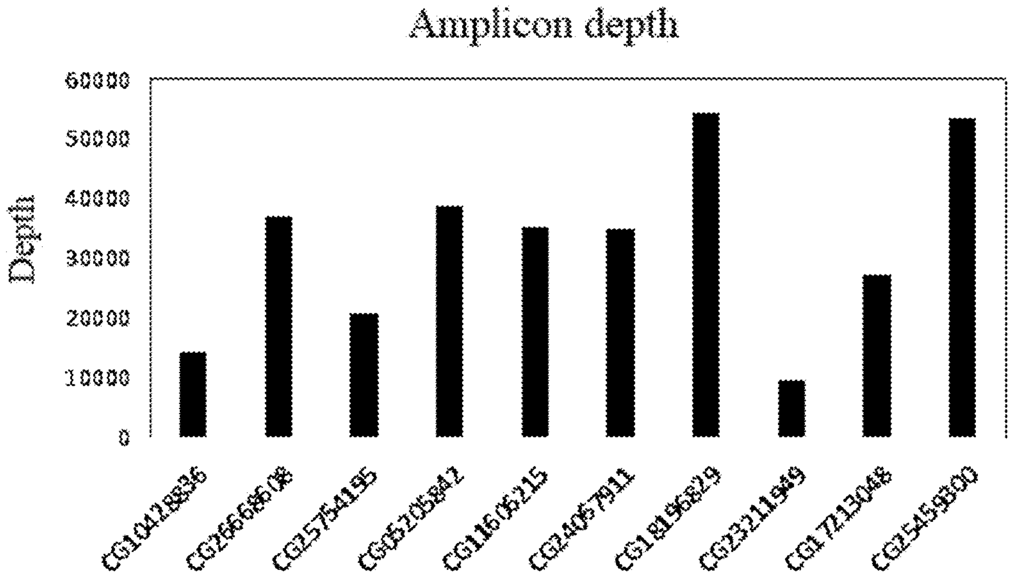
FIG. 7 is a graph illustrating results of sequencing depths of various amplicons according to an embodiment of the present disclosure.
Figure 8:
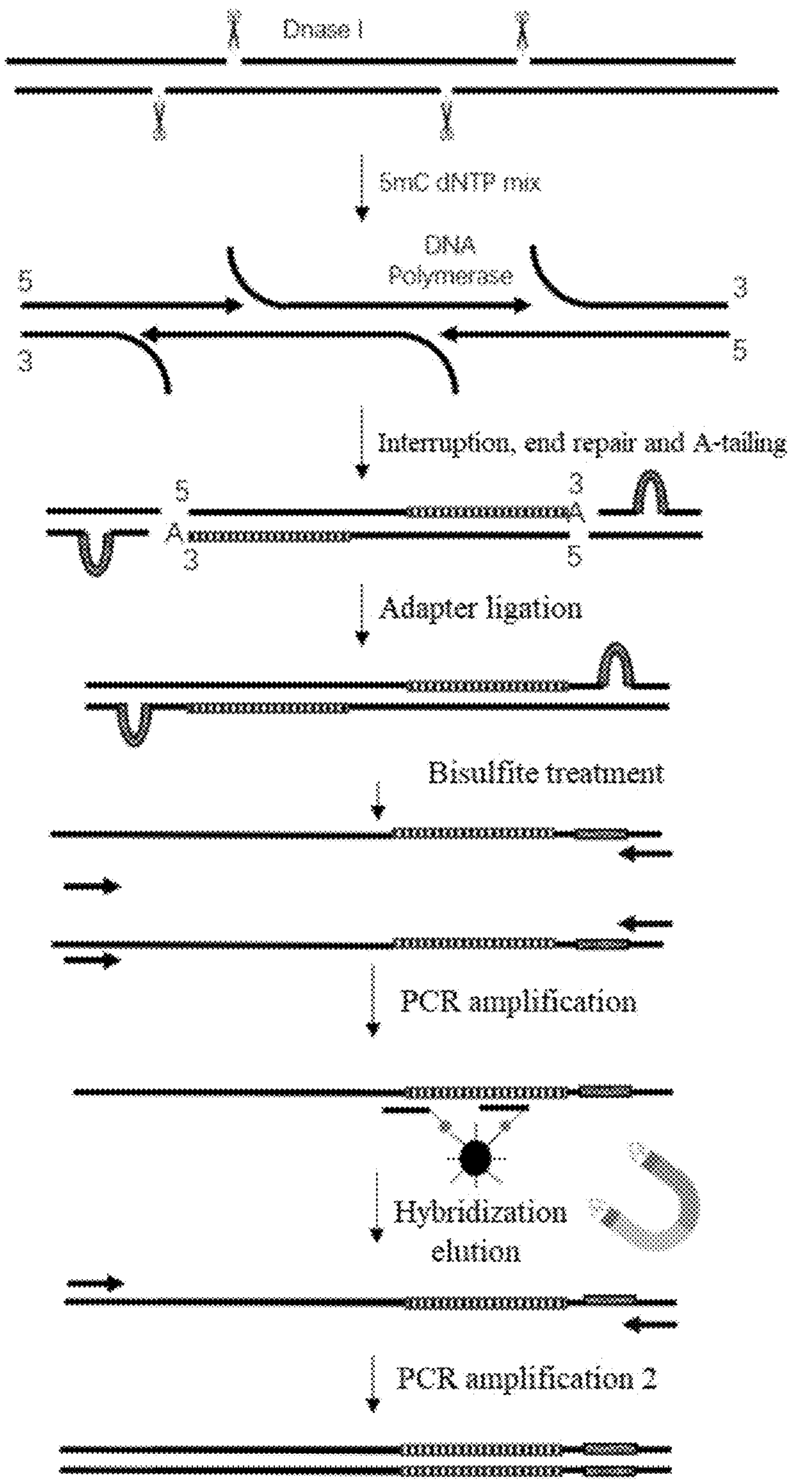
FIG. 8 is a flowchart of a DNA methylation hybrid library capture according to an embodiment of the present disclosure.

The results are shown in Table 2, and the depths of various amplicons are illustrated in FIG. 7.

TABLE 2

| | Sequencing data | | | | | |
|---|---|---|---|---|---|---|
| | Sequencing data | Mapping data | Mapping ratio | Targeting data | Specificity | Average depth |
| Method of the present disclosure | 71568006 | 70566054 | 98.6% | 65273600 | 92.5% | 32636 |

It can be seen from Table 2 that the method of the present disclosure has a good mapping ratio and a good specificity. In view of FIG. 7, the depths of the various amplicons have good uniformity.

TABLE 3

| Primer sequences | |
|---|---|
| Target CpG sites | Sequence |
| CG10428836-F01 (SEQ ID NO: 7) | ACATGGCTACGATCCGACTTGATGTGTTTGGGATATTGTTTATTTTATG |
| CG26668608-F02 (SEQ ID NO: 8) | ACATGGCTACGATCCGACTTTGTGTGTTGTGGTGAGGAGG |
| CG25754195-F03 (SEQ ID NO: 9) | ACATGGCTACGATCCGACTTAGGAGGGAAGGTTTGAGGTT |
| CG05205842-F04 (SEQ ID NO: 10) | ACATGGCTACGATCCGACTTGGTTAGTTGGAAGGAGTGGAAATT |
| CG11606215-F05 (SEQ ID NO: 11) | ACATGGCTACGATCCGACTTACGTGAAAGGGGAGAGGTA |
| CG24067911-F06 (SEQ ID NO: 12) | ACATGGCTACGATCCGACTTGGAGTTTTTTTGTGGGGTGAG |
| CG18196829-F07 (SEQ ID NO: 13) | ACATGGCTACGATCCGACTTGGTGGGGTAAAGGTGATTTTAG |
| CG23211949-F08 (SEQ ID NO: 14) | ACATGGCTACGATCCGACTTAGTTTTTTTAGATGTTGTGAATTGGGG |
| CG17213048-F09 (SEQ ID NO: 15) | ACATGGCTACGATCCGACTTTGTGGTGTAGTTAGAAGTGGTTT |
| CG25459300-F10 (SEQ ID NO: 16) | ACATGGCTACGATCCGACTTGGAGGGTTGGTAAAGTTTAGAAG |
| CG10428836-R01 (SEQ ID NO: 17) | CGCTTGGCCTCCGACTTCAAATGGCAGCAGAGGAATC |
| CG26668608-R02 (SEQ ID NO: 18) | CGCTTGGCCTCCGACTTGAATGGATGGCTTGGCCTG |
| CG25754195-R03 (SEQ ID NO: 19) | CGCTTGGCCTCCGACTTGTCTTCTAGTGGAAGAAGTGAAC |
| CG05205842-R04 (SEQ ID NO: 20) | CGCTTGGCCTCCGACTTGTCTGACTTAAGACTGGTGGC |
| CG11606215-R05 (SEQ ID NO: 21) | CGCTTGGCCTCCGACTTTCAGTGTACCTAACACAATATAGG |

TABLE 3-continued

| Primer sequences | |
|---|---|
| Target CpG sites | Sequence |
| CG24067911-R06 (SEQ ID NO: 22) | CGCTTGGCCTCCGACTTAGACATAGGTATGACAAGTTGCA |
| CG18196829-R07 (SEQ ID NO: 23) | CGCTTGGCCTCCGACTTCCTGATCCCAGGGTGCTG |
| CG23211949-R08 (SEQ ID NO: 24) | CGCTTGGCCTCCGACTTAGACCCAGTGACAAAATGCC |
| CG17213048-R09 (SEQ ID NO: 25) | CGCTTGGCCTCCGACTTCTTACTTAACCATTGTGTCCTTCCC |
| CG25459300-R10 (SEQ ID NO: 26) | CGCTTGGCCTCCGACTTCTCCAAAGAATGATTCCTCATTC |

The specific primer pool was an equimolar mixture of the above primers, and had a final concentration of 10 μM.

Example 3: Exon Methylation Region Capture Test 10 ng of gDNA was taken from Yanhuang cell line, and a library with a half retaining DNA methylation information and a half retaining DNA sequence information was prepared.

Then, the library was subjected to hybridization capture using MGI exon capture kit (MGIeasy Exome Capture V4 Probe Reagent, manufactured by MGI TECH CO., LTD., Cat. No. 1000007745). The captured library was delivered to MGIseq-2000 sequencer for sequencing, with sequencing type PE100 and sequencing depth 100X. Then, the data was analyzed, including analysis of data utilization, mapping ratio, GC bias and other properties. The experimental process is described below.

1. Interruption, End Repair and A-tailing;

The product was subjected to end repair and A-tailing reaction using NEB's Dnase I and BST. The reaction system and conditions are as follows.

| | |
|---|---|
| DNA | 37 μL |
| NEB buffer | 10 μL |
| Dnase I(0.4 U/μL) | 1 μL |
| BST | 1 μL |
| 5-mC dNTP mix (10 mM) | 1 μL |
| Total volume | 50 μL |

The above reaction system was placed on a PCR instrument, 37° C. for 10 minutes and 65° C. for 10 minutes. After the reaction was finished, purification was performed with 1.0X AMPure magnetic beads, and the purified product was dissolved in 20 μl of elution buffer.

2. Ligation of Methylated Adapters:

1) A ligation reaction system of the methylated adapters (also referred as to "methylation sequencing adapter") was prepared for the DNA obtained in the previous step:

| | |
|---|---|
| DNA | 18 μL |
| 2 × Rapid ligation buffer (Enzymatic) | 25 μL |
| Methylation sequencing adapter (100 uM)* (Baosheng biosynthesis) | 4 μL |
| T4 DNA ligase (Rapid, L603-HC-L Enzymatic) | 3 μL |
| Total volume | 50 μL |

-continued

The methylated adapter sequences are the same as those in Example 1, that is, set forth as SEQ ID NO: 1 and SEQ ID NO: 2.

3) The above reaction system was placed on a Thermomixer (Eppendorf) at 20° C., and reacted for 15 minutes to obtain a ligated product. After the reaction was finished, purification was performed with 1.0X AMPure magnetic beads, and the purified product was dissolved in 22 μl of elution buffer.

3. Bisulfite Treatment

The above ligated DNA was subjected to bisulfate co-treatment using EZ DNA Methylation-Gold Kit™ (ZYMO). The specific steps are as follows:

1) Preparation of CT conversion reagent solution: the CT conversion reagent (solid mixture) was taken out from the kit, added with 900 μL of water, 50 μL of M-dissolving buffer, and 300 μL of M-Dilution Buffer, dissolved at room temperature and oscillated for 10 minutes or shaken on a shaker for 10 minutes.

Preparation of M-washing buffer: 24 mL of 100% ethanol was added to M-washing buffer for later use.

2) 130 μL of CT conversion reagent solution and the ligated DNA were added to the PCR tube, and the sample was suspended by flicking or pipetting.

Then, the sample tube was placed on the PCR instrument to perform the following steps: 98° C. for 5 minutes, and 64° C. for 2.5 hours.

After the above operations were finished, the sample immediately proceeded to the next step or was stored at 4° C. (up to 20 hours) for later use.

3) The Zymo-Spin IC™ Column was placed into the collection tube, and 600 μL of M-Binding Buffer was added.

The bisulfite-treated sample was placed into the Zymo-Spin IC™ Column containing M-binding buffer, and the lid was closed and mixed evenly upside down.

Centrifugation was performed at full speed (>10,000×g) for 30 seconds, and the collected liquid in the collection tube was discarded.

100 μL of M-washing buffer was added to the column, followed by centrifugation at full speed (>10,000×g) for 30 seconds, and discarding the liquid in the collection tube.

200 μL of M-desulphonation buffer was added to the column and stood still at room temperature for 15 minutes, followed by centrifugation at full speed (>10,000×g) for 30 seconds, and discarding the liquid in the collection tube.

200 μL of M-washing buffer was added to the column, followed by centrifugation at full speed (>10,000×g) for 30 s, discarding the liquid in the collection tube, and repeating this step one more time.

The Zymo-Spin IC™ Column was placed in a new EP tube (1.5 mL), followed by adding 20 μL of M-elution buffer r to the column matrix, standing still at room temperature for 2 minutes, centrifugation at full speed (>10,000×g), and eluting the target fragment DNA.

4. PCR Amplification

According to the following system, a PCR reaction system was prepared with the target fragment DNA obtained in the previous step according to the following system, and the amplification enzyme system was KAPA HiFi HotStart Uracil+ReadyMix (2X) (from KAPA Biosystems, Cat. No. kk2801).

| | |
|---|---|
| Ligated DNA from the previous step | 20 μL |
| 2 × kapa HIFI hot start Uracil ready mix | 25 μL |
| Universal primer 1 (10 μM) | 2.5 μL |
| Universal primer 2 (10 μM) | 2.5 μL |
| Total volume | 50 μL |

The sequences of the universal primer 1 and the universal primer 2 are the same as those in Example 1, i.e., set forth as SEQ ID NO: 3 and SEQ ID NO: 4.

PCR reaction conditions:

| | | |
|---|---|---|
| 94° C. | 1 min | |
| 94° C. | 30 s | |
| 55° C. | 30 s | 12 cycles |
| 72° C. | 30 s | |
| 72° C. | 5 min | |
| 12° C. | maintained | |

After the reaction was finished, purification was performed with AMPure magnetic beads, and the purified product was dissolved in 22 μl of elution buffer.

5. Hybridization 1) 1000 ng of the PCR product was taken in accordance with the concentration of the PCR product. If multiple samples are required for mixed hybridization, at least 250 ng of each sample was input, and 1000 ng≤total input of PCR product≤2000 ng.

Preparation of Block mixture liquid (see Table 4):

TABLE 4

Preparation of Block mixture liquid

| Components | Single reaction volume |
|---|---|
| Block 1 | 2.5 μL |
| Block 2 | 2.5 μL |
| Block 3 | 1 μL |
| Block 4 | 10 μL |
| Total | 16 μL |

2) 16 μL of the prepared Block mixture was pipetted with a pipette and added into the sample to prepare a pre-hybridization mixture liquid, which was then placed in a concentrator and concentrated to 9 μL. If the volume was smaller than 9 μL, the volume was made up to 9 μL with NF water.

3) 9 μL of the pre-hybridization mixture liquid was placed on the PCR instrument, and pre-hybridization was performed according to the reaction conditions listed in Table 5:

TABLE 5

Pre-hybridization reaction conditions

| Temperature | Time |
|---|---|
| Hot lid | On |
| 95° C. | 5 min |
| 65° C. | Hold |

6. Hybrid Capture

1) A hybridization mixture liquid was prepared in a new 0.2 mL PCR tube (see Table 6).

TABLE 6

Preparation of hybridization mixture liquid

| Components | Single reaction volume |
|---|---|
| Hyb Buffer 1 | 10 μL |
| Hyb Buffer 2 | 0.4 μL |
| Hyb Buffer 3 | 4 μL |
| Hyb Buffer 4 | 5.6 μL |
| Total | 20 μL |

2) The hybridization mixture liquid was incubated in a PCR instrument at 65° C. for at least 5 minutes, and the system can be used only after it was confirmed through light observation that no crystal precipitation was present in the system.

3) A new 96-well PCR plate (recommended) was taken to prepare the probe mixture liquid on ice (see Table 7).

TABLE 7

Preparation of probe mixture liquid

| Components | Volume |
|---|---|
| NF water | 1.5 μL |
| Block 5 | 0.5 μL |
| MGI Exome V4 Probe | 5 μL |
| Total | 7 μL |

4) The probe mixture liquid was placed on the PCR instrument and incubated according to the reaction conditions in Table 8.

TABLE 8

Incubation of probe mixture liquid

| Temperature | Time |
|---|---|
| Hot lid | On |
| 65° C. | 2 min |
| 65° C. | Hold |

5) The above various mixture liquids were kept at 65° C., and 13 μL of the hybridization mixture liquid was quickly sucked and transferred to 9 μL of the pre-hybridization mixture liquid, and mixed evenly by pipetting.

6) The various mixture liquids were kept at 65° C., the 22 μL of the liquid prepared in the previous step was quickly transferred to the probe mixture liquid, and mixed evenly by pipetting.

7) The PCR plate was quickly sealed with a high-transmittance adhesive cover film, the sealing film was pressed tightly to ensure that all the wells were completely sealed, and this step was repeated once (i.e., seal the film twice).

8) The 96-well PCR plate was kept at 65° C., and the hybridization reaction was performed in accordance with the reaction conditions in Table 9 for 24 hours.

TABLE 9

| Hybridization reaction conditions | |
|---|---|
| Temperature | Time |
| Hot lid (105° C.) | On |
| 65° C. | Hold |

7. Preparation Before Elution

1) The Thermomixer was adjusted to 65° C. at least 30 minutes in advance, and 1.8 mL of Wash Buffer II was placed in a 2.0 mL centrifuge tube, which was then preheated to 65° C. in the Thermomixer.

2) M-280 magnetic beads were oscillated and mixed thoroughly, and 50 μL of the M-280 magnetic beads was transferred into a new 2.0 mL centrifuge tube by a pipette.

3) 200 μL of binding buffer was added and vortex-shaken for 5 seconds until all the magnetic beads were suspended.

4) The centrifuge tube was centrifuged instantaneously and stood still on a magnetic stand for 2 minutes to 5 minutes until the liquid was clear, followed by carefully pipetting the supernatant.

5) The above steps were repeated twice.

6) 200 μL of binding buffer was added to resuspend the magnetic beads.

8. Elution

1) After 24 hours of incubation, the hybridization reaction solution was kept on the PCR instrument at 65° C., the sealing film was cut with a razor blade, the remaining hybridization solution was quickly aspirated with a pipette to estimate a volume thereof, and then the remaining hybridization solution was transferred to the centrifuge tube containing 200 μL of the magnetic beads from the previous step.

2) The centrifuge tube was placed on a Nutator or a similar device and evenly mixed by rotating 360°, and incubated at room temperature for 30 minutes with rotation.

3) The sample was removed from the Nutator.

4) The centrifuge tube was centrifuged instantaneously and stood still for 2-5 minutes on a magnetic stand until the liquid was clear, and the supernatant was carefully aspirated and discarded with a pipette.

5) 500 μL of Wash Buffer I was added, all the magnetic beads are suspended by turning upside down, and incubated for 15 min at room temperature.

6) The centrifuge tube was centrifuged instantaneously and stood still for 2-5 minutes on a magnetic stand until the liquid was clear, and the supernatant was carefully aspirated and discarded with a pipette.

7) 500 μL of pre-heated Wash Buffer II was added to the centrifuge tube, the centrifuge tube was placed in the Thermomixer, the rotation speed was adjusted to 1000 rpm to oscillate for 10 seconds to suspend all the magnetic beads. Then, the rotation speed was adjusted to 0 rpm, the temperature was adjusted to 65° C., and the centrifuge tube stood still and incubated for 10 minutes.

8) The centrifuge tube was centrifuged instantaneously and stood still for 30 seconds on a magnetic stand until the liquid was clear, and the supernatant was carefully aspirated and discarded with a pipette.

9) Steps 7 to 8 were repeated twice.

10) The magnetic beads were resuspended with 100 μL of NF water, all the resuspended sample (including magnetic beads) was transferred to a new 1.5 mL centrifuge tube, and the new centrifuge tube was centrifuged instantaneously.

11) The 1.5 mL centrifuge tube was placed on the magnetic stand and stood still for 2 minutes until the liquid was completely clear, and the supernatant was carefully aspirated and discarded with a pipette with small measurement range, repeating the aspiration to ensure that no liquid remained.

12) The magnetic beads were resuspended with 44 μL of NF water, and all the resuspended sample (including magnetic beads) was transferred to a new PCR tube with a pipette.

9. PCR After Hybridization

1) The PCR reaction solution after hybridization was prepared on ice (see Table 10):

TABLE 10

| Preparation of PCR reaction solution after hybridization | |
|---|---|
| Components | Single reaction volume |
| Post-PCR Enzyme Mix | 50 μL |
| PCR Primer Mix | 6 μL |
| Total | 56 μL |

2) 56 μL of the prepared PCR reaction solution was aspirated with a pipette and added into a PCR tube containing the magnetic beads, and vortexed and oscillated 3 times, 3 seconds each time, and the reaction solution was collected to the bottom of the tube by instant centrifugation.

3) The PCR tube was placed on the PCR instrument, and the PCR after hybridization was performed under the conditions listed in Table 11:

TABLE 11

| PCR reation conditions afer hybridization | | | |
|---|---|---|---|
| Temperature | Time | Number of cycles | |
| Heated lid | on | | |
| 95° C. | 3 min | 1 | cycle |
| 98° C. | 20 s | 13 | cycles |
| 60° C. | 15 s | | |
| 72° C. | 30 s | | |
| 72° C. | 10 min | 1 | cycle |
| 4° C. | Hold | | |

9. Library Detection:

The size and content of inserts of the library were detected with Bioanalyzer analysis system (Agilent, Santa Clara, USA). As such, the constructed high-throughput sequencing library of the specific region of the genome of the sample was detected.

10. Sequencing

The obtained library was subjected to high-throughput sequencing on sequencing platform MGIseq-2000, with sequencing type PE100, and the sequencing data was subjected to alignment to statistically analyze various basic parameters, including sequencing data, mapping data, ratio of target region, etc.

11. Results

Figure 9:
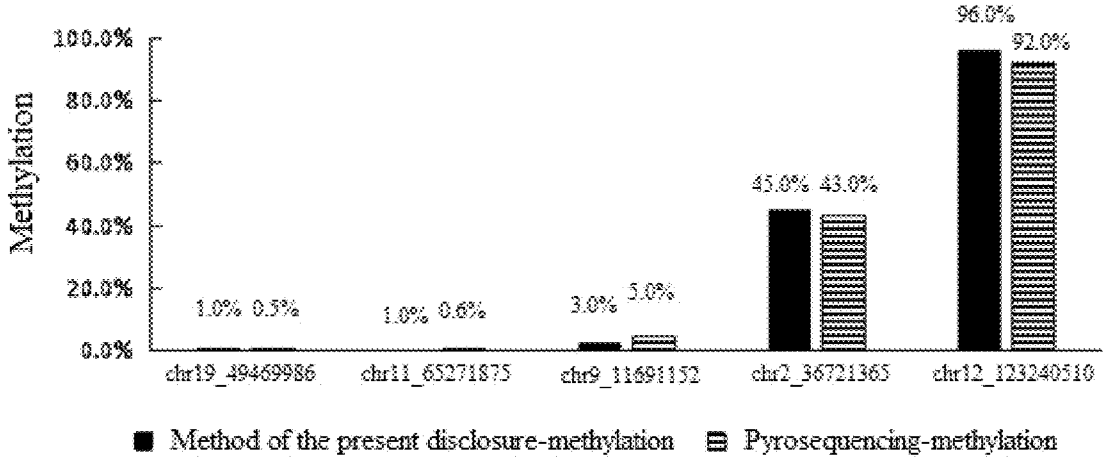
FIG. 9 is a graph of a comparison result on a methylation rate of target sites provided according to an embodiment of the present disclosure.

The basic parameter statistics obtained by the method of the embodiment of the present disclosure are shown in Table 12;

FIG. 9 illustrates the comparison between the methylation rate of the target sites obtained by the method of the embodiment of the present disclosure and the methylation rate obtained by pyrophosphate.

TABLE 12

| Sample name | Count of Reads | Mapping ratio | Repetition rate | Capture rate | Average depth | 20X Coverage |
|---|---|---|---|---|---|---|
| Sample 1 | 167912362 | 89.09% | 21.06% | 49.08% | 99.47 | 95.20% |
| Sample 2 | 173037720 | 86.16% | 19.84% | 50.84% | 99.13 | 94.98% |
| Sample 3 | 165932310 | 88.11% | 20.44% | 48.68% | 99.67 | 95.17% |

In Table 12, the mapping ratio refers to a ratio of mapping to the genome, the repetition rate refers to a proportion of measured reads at the same position, the capture rate refers to a ratio of reads mapped to the target region to the total reads, the average depth refers to an average depth of the target regions covered by the sequencing, and the 20× coverage refers to a proportion of the target regions covered by sequencing reads 20×.

After the sequencing, the sequencing data was aligned to the DNA sequences and the methylation sequences, the obtained mapping data (87.8%) was then used to statistically analyze the data falling in the exon region and flanking region (49.5%), and the average depth (99.3×) and 20× coverage (95.2%) of the target region were statistically analyzed. It is obvious that this method of the present disclosure can effectively conduct the methylation capture.

In the specification, the terms "first", "second", etc., are only used for descriptive purposes, and cannot be understood as indicating or implying relative importance or implicitly indicating the number of indicated technical features. Thus, the features defined with "first" and "second" may explicitly or implicitly include at least one of the features. In the specification, "multiple" means at least two, such as two, three, etc., unless otherwise specifically defined.

In the specification, descriptions with reference to the terms such as "one embodiment", "some embodiments", "examples", "specific examples", and "some examples" indicate that specific features, structures, materials or characteristics described in conjunction with the embodiment or example are included in at least one embodiment or example of the present disclosure. In this specification, the schematic representations of the above-mentioned terms are not necessarily directed to the same embodiment or example. Moreover, the described specific features, structures, materials or characteristics can be combined in any one or more embodiments or examples in a suitable manner. In addition, those skilled in the art can combine and integrate the different embodiments or examples and the features of the different embodiments or examples described in this specification, as long as they do not contradict each other.

Although the embodiments of the present disclosure are illustrated and described above, it can be understood that the above-mentioned embodiments are exemplary and should not be construed as limiting the present disclosure. Those skilled in the art can make changes, modifications, substitutions, and variants to the embodiments within the scope of the present disclosure.

What is claimed is:

1. A method for determining a methylation state of a DNA sample, the method comprising:

constructing a sequencing library based on the DNA sample;

sequencing the sequencing library to obtain sequencing results of the DNA sample;

aligning the sequencing results of a 5'-end and a 3'-end of the DNA sample respectively with a reference genome to determine position information of the 5'-end and the 3'-end; and analyzing a position of the DNA sample by comparison based on the position information of the 5'-end and the 3'-end to determine the methylation state of the DNA sample, wherein said constructing a sequencing library based on the DNA sample comprises:

digesting the DNA sample with endonuclease to obtain a DNA sample with single-strand nicks;

polymerizing the DNA sample with the single-strand nicks by using polymerase, dATP, dTTP, dGTP, and methylated dCTP to obtain a hybrid DNA, wherein the hybrid DNA comprises two strands that are reversely complementary to each other, a 5'-end sequence of each of the two strands is an original sequence of the DNA sample, a 3'-end sequence of each of the two strands is a synthetic sequence, and all bases C at the 3'-end sequence of each of the two strands are methylated;

ligating a methylation sequencing adapter to the hybrid DNA, wherein the methylation sequencing adapter comprises a first universal sequence and a second universal sequence;

subjecting the hybrid DNA to a bisulfite treatment to obtain a converted hybrid DNA; and amplifying the converted hybrid DNA using universal primers to obtain the sequencing library, wherein the universal primer matches the first universal sequence and the second universal sequence.

2. The method according to claim 1, wherein said aligning the sequencing results of a 5'-end and a 3'-end of the DNA sample respectively with a reference genome to determine position information of the 5'-end and the 3'-end comprises:

when the 3'-end corresponds to multiple candidate positions, the 5'-end corresponds to one candidate position, and a position adjacent to the candidate position corresponding to the 5'-end is one of the multiple candidate positions corresponding to the 3'-end, determining the position information of the 5'-end and the 3'-end based on the candidate position corresponding to the 5'-end;

when the 3'-end corresponds to multiple candidate positions, the 5'-end corresponds to multiple candidate positions, determining the position information of the 5'-end and the 3'-end based on a common optimal candidate position of the 5'-end and the 3'-end;

when the 3'-end corresponds to one candidate position, the 5'-end corresponds to multiple candidate positions, and a position adjacent to the candidate position corresponding to the 3'-end is one of the multiple candidate positions corresponding to the 5'-end, determining the position information of the 5'-end and the 3'-end based on the candidate position corresponding to the 3'-end;

when the 3'-end corresponds to one candidate position, the 5'-end corresponds to one candidate position, and a position adjacent to the candidate position corresponding to the 3'-end is adjacent to the candidate position of the 5'-end, determining the position information of the 5'-end and the 3'-end based on the candidate position corresponding to the 3'-end or the candidate position corresponding to the 5'-end; and determining a position to which the 3'-end is mapped as a main mapping position in other cases.

3. The method according to claim 1, wherein the 3'-end is aligned with the reference genome using BWA software, and the 5'-end is aligned with the reference genome using BS-map software.

4. The method according to claim 1, wherein the endonuclease is Dnase I, Dnase II, or any endonuclease capable of producing the single-strand nicks.

5. The method according to claim 1, wherein the DNA sample with the single-strand nicks has a length of 100 bp to 1000 bp.

6. The method according to claim 1, wherein the DNA sample is a whole genome DNA sample.

7. A method for determining a methylation state of a DNA sample, the method comprising:

constructing a sequencing library based on the DNA sample;

sequencing the sequencing library to obtain sequencing results of the DNA sample;

aligning the sequencing results of a 5'-end and a 3'-end of the DNA sample respectively with a reference genome to determine position information of the 5'-end and the 3'-end; and analyzing a position of the DNA sample by comparison based on the position information of the 5'-end and the 3'-end to determine the methylation state of the DNA sample, wherein said constructing a sequencing library based on the DNA sample comprises:

digesting the DNA sample with endonuclease to obtain a DNA sample with single-strand nicks;

polymerizing the DNA sample with the single-strand nicks by using polymerase, dATP, dTTP, dGTP, and methylated dCTP to obtain a hybrid DNA, wherein the hybrid DNA comprises two strands that are reversely complementary to each other, a 5'-end sequence of each of the two strands is an original sequence of the DNA sample, a 3'-end sequence of each of the two strands is a synthetic sequence, and all bases C at the 3'-end sequence of each of the two strands are methylated;

subjecting the hybrid DNA to a bisulfite treatment to obtain a converted hybrid DNA; and amplifying the converted hybrid DNA using specific primers to obtain a sequencing library based on a target region of the DNA sample, wherein the specific primers comprise first specific primers and second specific primers, the first specific primers are located at 5'-ends of the converted hybrid DNA, and the second specific primers are located at 3'-ends of the converted hybrid DNA.

8. The method according to claim 1, wherein said constructing a sequencing library based on the DNA sample further comprises:

hybrid capturing the converted hybrid DNA by using a probe and eluting to obtain a captured product, wherein the probe is configured to hybridize a 3'-end sequence of the converted hybrid DNA; and amplifying the captured product to obtain the sequencing library.

* * * * *